(12) United States Patent  
Fakhrai

(10) Patent No.: US 7,824,332 B2  
(45) Date of Patent: Nov. 2, 2010

(54) RETRACTOR

(75) Inventor: Mehdi Fakhrai, 3457 Alana Dr., Sherman Oaks, CA (US) 91403

(73) Assignee: Mehdi Fakhrai, Sherman Oaks, CA (US)

( * ) Notice: Subject to any disclaimer, the term of this patent is extended or adjusted under 35 U.S.C. 154(b) by 504 days.

(21) Appl. No.: 11/328,886

(22) Filed: Jan. 11, 2006

(65) Prior Publication Data

US 2007/0161865 A1    Jul. 12, 2007

(51) Int. Cl.  
*A61B 1/32* (2006.01)

(52) U.S. Cl. .................. 600/232; 600/217; 600/218; 600/219; 600/231

(58) Field of Classification Search ......... 600/231–233; 606/105  
See application file for complete search history.

(56) References Cited

U.S. PATENT DOCUMENTS

| | | | | |
|---|---|---|---|---|
| 1,456,116 | A * | 5/1923 | Bessesen, Sr. ............... | 600/232 |
| 2,670,731 | A * | 3/1954 | Zoll et al. ................... | 600/232 |
| 2,807,259 | A * | 9/1957 | Federico ..................... | 600/222 |
| 3,749,088 | A * | 7/1973 | Kohlmann ................... | 600/234 |
| 4,627,421 | A * | 12/1986 | Symbas et al. .............. | 600/232 |
| 4,852,552 | A * | 8/1989 | Chaux ........................ | 600/232 |
| 5,052,373 | A * | 10/1991 | Michelson .................. | 600/217 |
| 5,088,472 | A * | 2/1992 | Fakhrai ...................... | 600/214 |
| 5,365,921 | A * | 11/1994 | Bookwalter et al. ......... | 600/232 |
| 5,730,757 | A * | 3/1998 | Benetti et al. ............... | 606/198 |
| 5,772,583 | A * | 6/1998 | Wright et al. ............... | 600/232 |
| 5,865,731 | A * | 2/1999 | Lenox et al. ................ | 600/232 |
| 5,984,867 | A * | 11/1999 | Deckman et al. ............ | 600/232 |

* cited by examiner

*Primary Examiner*—Thomas C Barrett  
*Assistant Examiner*—Andrew Yang

(57) ABSTRACT

The invention is a sternal retractor comprising a pair of arms each of which includes a downward extending blade, and one of which includes a proximal portion and a distal portion pivotally mounted on the proximal portion, a curved cross bar on which said arms are disposed so that in use the retractor can open the bottom of the sternum wider than the top of the sternum to minimize damage to the upper ribs and numbness, which sometimes occurs in the hands of open chest surgery patients. The retractor also has applications within other surgical procedures, as well, for the same general purpose of providing an opening of varying size along the length of an incision.

2 Claims, 5 Drawing Sheets

RETRACTOR

BACKGROUND OF THE INVENTION

1. Field of the Invention

This invention relates to the field of medical surgical tools, and more particularly, to retractors for chest surgery.

2. Art Background

In open chest surgery, and particularly for cardiac surgery, the sternum is split with chest saw and is held open by a retractor. The sternum is a short bone in the middle of the chest to which all of the ribs are attached either directly, or indirectly. The ribs attached to the top of the sternum are shorter than the ribs attached to the bottom of the sternum. Accordingly, when the chest is opened using the retractor, more stress is placed on the shorter upper ribs than the longer lower ribs, as explained in more detail below. Such stress causes various problems including broken ribs.

Typical prior art retractors, also termed sternal spreading or chest spreading retractors, comprise two elongated metal members, termed arms, with blades disposed thereon to capture the sternum, the arms being parallel to each other, and a rack or bar with teeth on which the arms are disposed. One of the arms is fixed in position for moving the other arm along the rack. The prior art retractors opened so that the arms remain parallel with respect to each other throughout their range of motion. Accordingly, in use, the sternum was displaced an equal amount along the entire length of the retractor. Prior art retractors include those devices which have long blades, short blades, multiple short blades or bent arms. Also, for pediatric and small patients, a small sized retractor of the same general configuration as described above may be used.

One recent prior art device comprises a pair of blades which are pivotable through the plane defined by the blades and the bar connecting them. This device is intended to provide pressure evenly along the entire sternum and it opens in a generally triangular configuration as opposed to the generally rectangular configuration. However, the device does not provide positive control of the movement of the sternum as it is opened and does not necessarily open the sternum to a desired position. The device is described in U.S. Pat. No. 4,627,421 issued to Symbas et al.

Another prior art device described in Chaux et al., U.S. Pat. No. 4,852,552 comprises a sternal retractor with blades which rotate in two different axes to permit one portion of the split sternum to be raised above the other portion in order to provide access to particular portions of the chest cavity.

It has been observed that as a result of the use of such prior art devices, that following the surgery, a substantial percentage of patients develop a neuropathy in which numbness occurs in their left or right hand, and specifically, in the fourth and/or fifth digits (the ring finger and little finger). This numbness usually disappears after a while, but it has been known to occur for a substantial period of time, and in any event, such numbness is at best annoying to the surgical patients. The apparent cause of this numbness is that in opening the chest, the opening of the ribs puts substantial pressure on the lower branch of the brachial plexus. The lower ribs are longer and also have more cartilage which permits them to be spread more easily and with less risk than the upper ribs. Also, the lower ribs are not connected to any neurologically important portion of the plexus.

One method of overcoming this problem of applying excessive pressure to the upper ribs and the adjacent portion of the plexus has been for the surgeon to attempt to position the retractor as low as possible so that there is minimal pressure on the upper, shorter ribs. However, this approach is not particularly desirable because the surgeon is not able to position the retractor in the most advantageous position for retraction of the chest. The present invention overcomes the foregoing deficiencies of the prior art devices and methods.

SUMMARY OF THE INVENTION

The present invention is a retractor of the general type found in the prior art with certain improvements therein which eliminate the problem which occurs during cardiac or other open chest surgery wherein numbness of the fourth and fifth digits of the right and/or left hand is caused when the chest is opened and held open with the prior art retractors and methods. The present invention also minimizes the risk of breaking ribs, particularly the shorter ribs, during such surgery.

The present invention comprises a retractor, a specifically a sternal spreader, having two arms with blades disposed on each arm, said arms being disposed on a cross bar, sometimes referred to as a rack. The invention specifically comprises the cross bar being curved rather than straight, as is provided in the prior art. The arms remain generally perpendicular to the cross bar as they moved along the cross bar closer to and away from each other, but in view of the curvature of the cross bar, one end of the arms is always closer to each other than the other end of the arms.

Preferably, for an adult sternal spreader, when the end of the arms adjacent with the short ribs is approximately 4 inches apart, the end of the arms adjacent the long ribs is approximately 8 inches apart. Also preferably, the curvature of the cross bar is approximately 40 degrees. Of course the curvature of the cross bar can be varied considerably, the important feature being that the arms spread apart to form a generally triangularly-shaped opening in the chest as the sternum is spread apart. Any form of attachment means for attaching the arms to the cross bar and moving the arms along the cross bar may be employed, the preferred system comprising a rack and pinion.

In accordance with one aspect of the invention, a surgical sternal retractor is provided, including a bar, and a pair of arms mounted on the bar. At least one of the arms is mounted to slide along the bar and to be locked in place on the bar. Each of the arms includes a blade extending downward along the arm from a proximal end of the blade to a distal end of the blade at a distal end of the arm. At least one of the arms includes a proximal portion mounted on the bar and a distal portion mounted by a hinge to pivot on the proximal portion between the proximal end of the blade and the bar.

Preferably, the bar is curved so that proximal and distal ends of the blades of the pair of arms are additionally separated by different distances as the arms are moved apart, with the arms being configured for mounting to extend from the bar in a first direction or opposite the first direction. Preferably, the bar includes gear teeth extending along a first side and a side opposite the first side, with at least one of the arms including a rotatably mounted pinion engaging the teeth extending along the first side of the bar with the arms mounted to extend from the bar opposite the first direction, and engaging the teeth extending along the side of the bar opposite the first side with the arms mounted to extend from the bar opposite the first direction.

In accordance with another aspect of the invention, a method for sternal retraction is provided, including: inserting blades extending downward from arms within a sternal retractor into a split within the sternum; spreading the arms within the sternal retractor through a short distance to begin sternal retraction; rotating a distal portion of one of the arms, including one of the blades; about a pivot point attaching the distal portion of the arm to a proximal portion of the arm; locking the distal portion in place on a proximal portion of the arm including the distal portion; and spreading the arms within the sternal retractor further to complete sternal retraction. For example, the distal portion is rotated toward the other arm with the bar located near the abdomen of the patient, and with the bar being curved so that, as the arms are spread apart, the distal ends of the blades are spread apart through a first distance, and the proximal ends of the blades are spread apart through a distance greater than the first distance.

It is an object of the present invention to provide a retractor which is structurally simple and which does not obstruct the surgeon's view of the chest cavity, and particularly which does creates the largest possible viewing area with a minimal amount of trauma to the ribs.

It is another object of the present invention to provide a retractor which minimizes injury to the brachial plexus during open chest surgery.

It is another object of the present invention to provide a retractor which minimizes the risk of broken ribs, particularly the shorter ribs.

It is another object of the present invention to provide a retractor which can be used in a plurality of configurations with the cross bar being disposed either above or below the surgical area.

It is yet another object of the present invention to provide a retractor which can be provided a variety of sizes and curvatures and with a variety in the number of blades, as required.

These and other objects of the present invention are achieved by providing a retractor which is shown in several presently preferred embodiments in the drawings which are described briefly below.

DETAILED DESCRIPTION OF THE INVENTION

Figure 1:
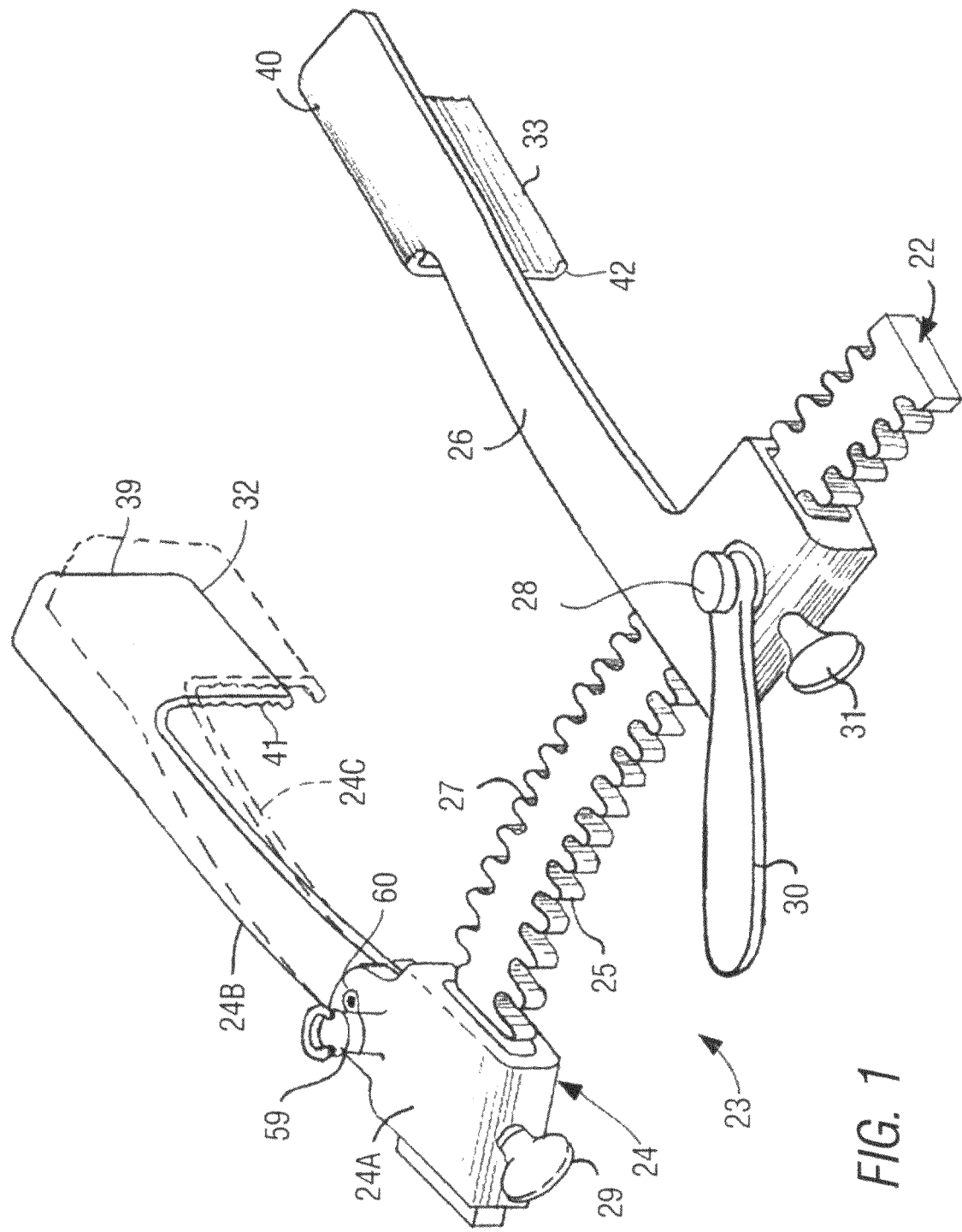
FIG. 1 is a perspective view of a retractor built in accordance with a preferred embodiment of the present invention assembled in a first configuration.
Figure 3:
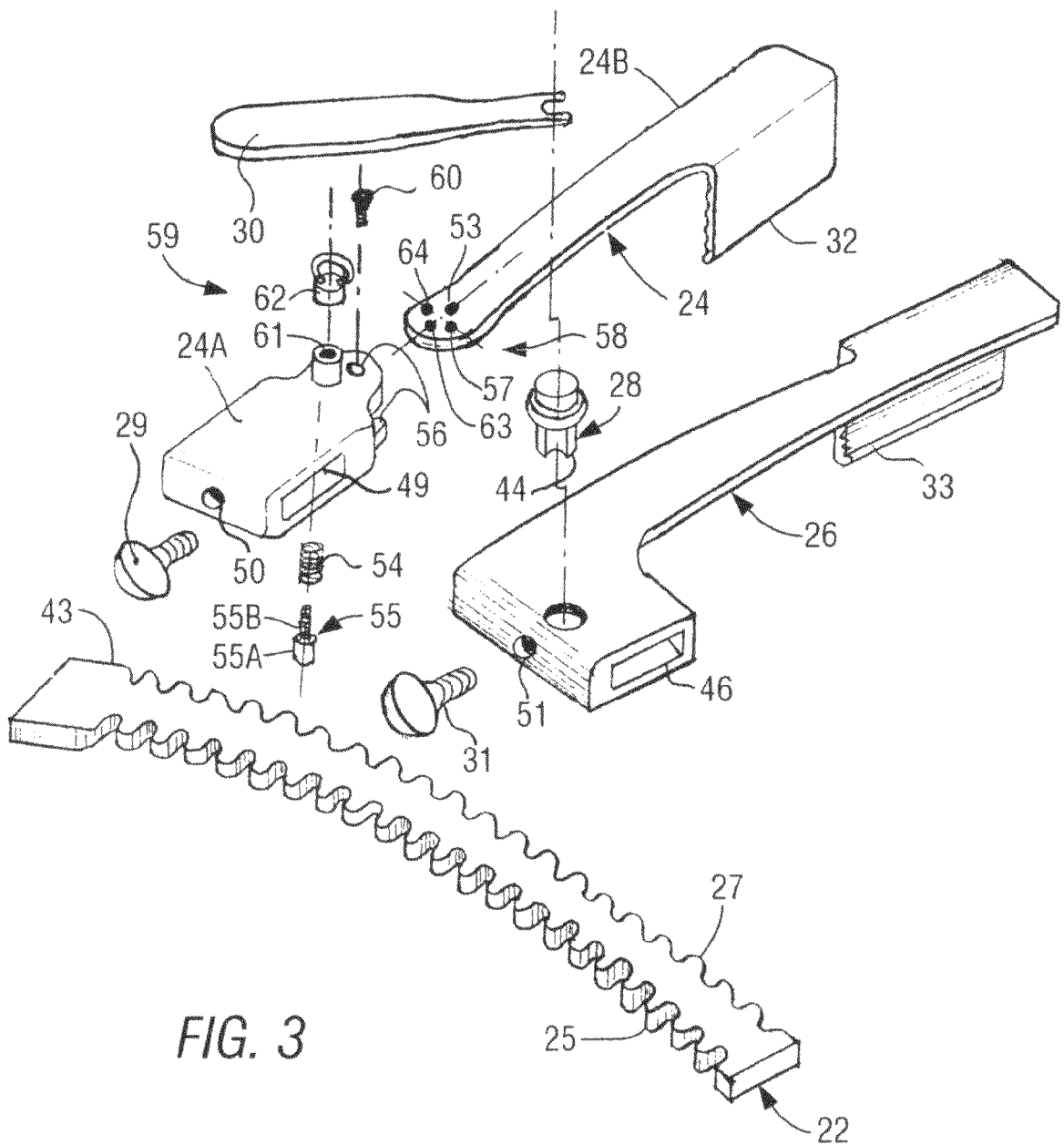
FIG. 3 is a perspective exploded view of the retractor of FIG. 1.
Figure 4:
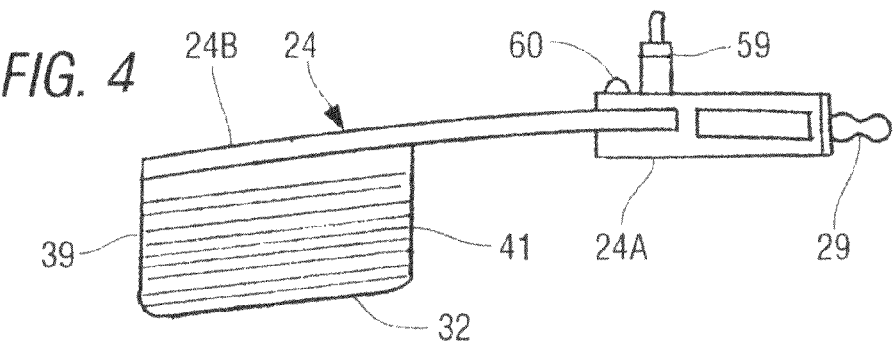
FIG. 4 is a side view of a first arm within the retractor shown in FIG. 2.
Figure 6:
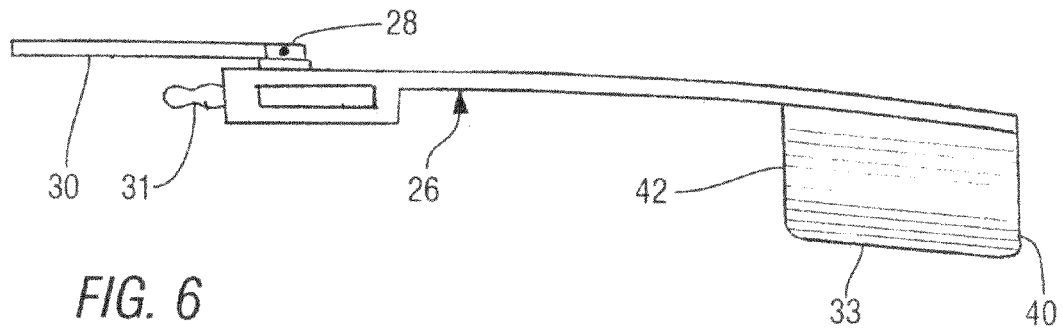
FIG. 6 is a side view of the a second arm within the retractor shown in FIG. 1.
Figure 7:
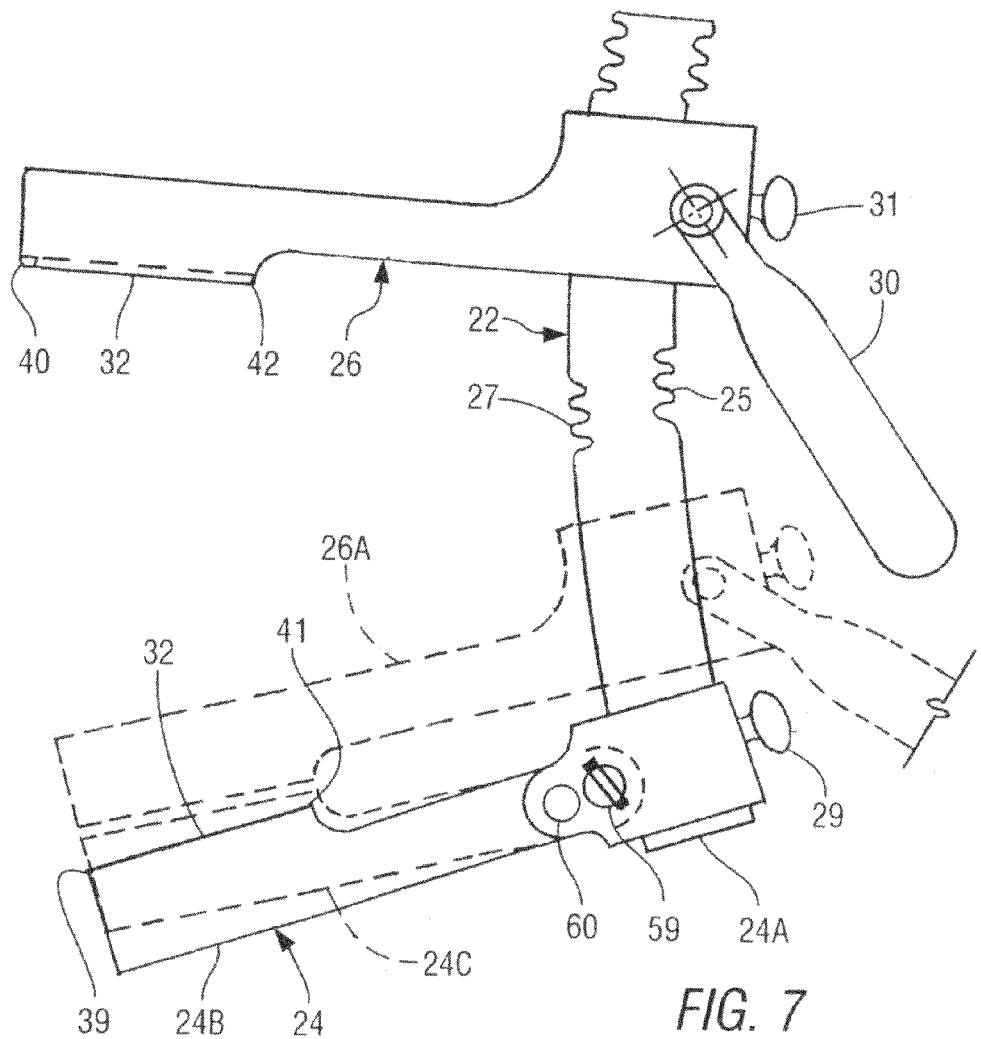
FIG. 7 is a plan view of the retractor assembled as shown in FIG. 1.

As shown in FIGS. 1, 3, 4, 6, and 7, a retractor 23 of the present invention comprises generally a cross bar or rack 22, a first arm 24, comprising a proximal portion 24A and a distal portion 24B, and second arm 26. FIG. 1 is a perspective view of the retractor 23, while FIG. 3 is an exploded perspective view thereof. FIGS. 4 and 6 are side views of the first arm 24 and the second arm 26, respectively. FIG. 7 is a plan view of the retractor 23 assembled as shown in FIG. 1. The distal portion 24B of the first arm 24 is pivotally connected to the proximal portion 24A thereof by a hinge 59 and is further held in position by a locking mechanism 60. When the locking mechanism 60 is released, the distal portion 24B may be rotated about the hinge 59 to be locked in a new position. For example, the distal portion 24B can be rotated between a medial position, in which it is shown in FIG. 1, and an inward position, indicated by dashed lines 24C. The cross bar 22 has, in the preferred embodiment, teeth on two opposing surfaces 25 and 27 for reasons that will be explained below. The cross bar 22 is curved so that the arms 24 and 26 are not parallel to each other when the arms are opened or spread apart, but are angled outward away from each other as shown in FIG. 1. The distal portion 24B of the first arm 24 includes a downwardly extending blade 32, and the second arm 26 includes a downwardly extending blade 33.

When the arms are closed to be adjacent to each other with the distal portion 24B of the of the first arm 24 held in the inward position, in which it is shown with dashed lines in FIG. 1, by the locking mechanism 60, the distal portion 24B of the first arm 24 and the second arm 26 are substantially parallel to each other, facilitating the insertion of the blades 32, 33 into an open sternum. One, or possibly both, of the arms 24, 26 may be moved along the bar 22 preferably by a moving means comprising a pinion 28 driven by a handle 30. This arrangement allows the present invention to be installed and to force the severed portions of the sternum apart. The arms have disposed thereon blades 32 and 33, which are common to prior art chest separators, and which are adapted to secure the sternum after it is severed. The present invention includes the use of blades which are longer than those depicted as well as multiple blades on a single arm, and angled arm blades, all of which is well known in the art, and after a short distance opening the fixed arm will be moved to straight (neutral) position and held in place by pin spring 60 and, continued to the desired opening.

FIGS. 1 and 7 are views of the retractor 23 assembled in a first configuration, for use with the bar 22 disposed closer to the head of a patient than to the abdomen. FIG. 1 is a perspective view of the retractor 23 so assembled, while FIG. 7 is a plan view thereof. with the distal end 39 of the blade 32 and the distal end 40 of blade 33 being further apart than their proximal ends 41, 42. Accordingly, as used in the configuration of FIG. 1, the retractor 23 positively forces the sternum into a specific angled position dictated by the curvature of the bar 22 and the distance between the arms 24. 26. In this way the chest opening can be small at area adjacent the short ribs and larger at the area adjacent the longer ribs.

Figure 2:
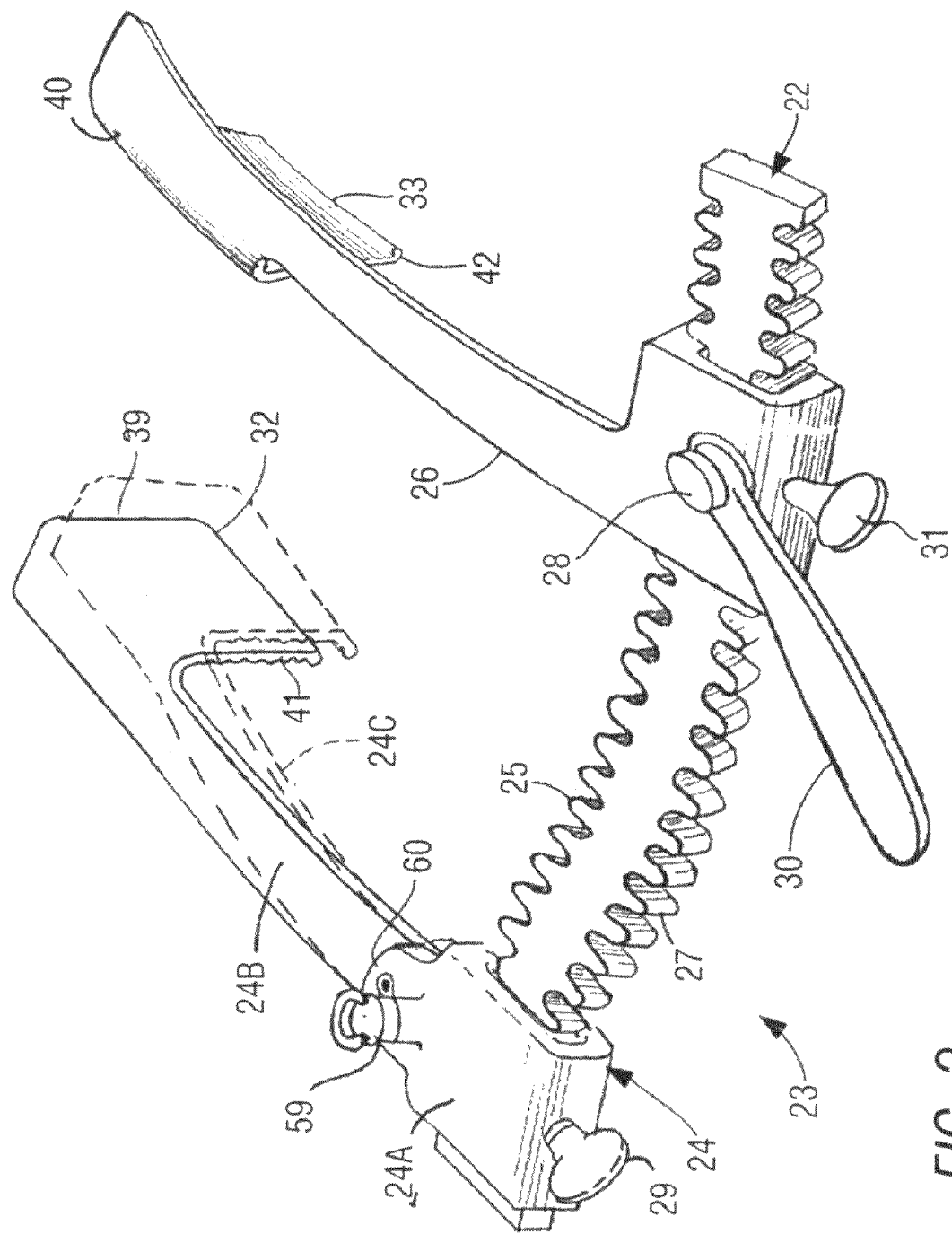
FIG. 2 is a perspective view of the retractor of FIG. 1 assembled in a second configuration.
Figure 5:
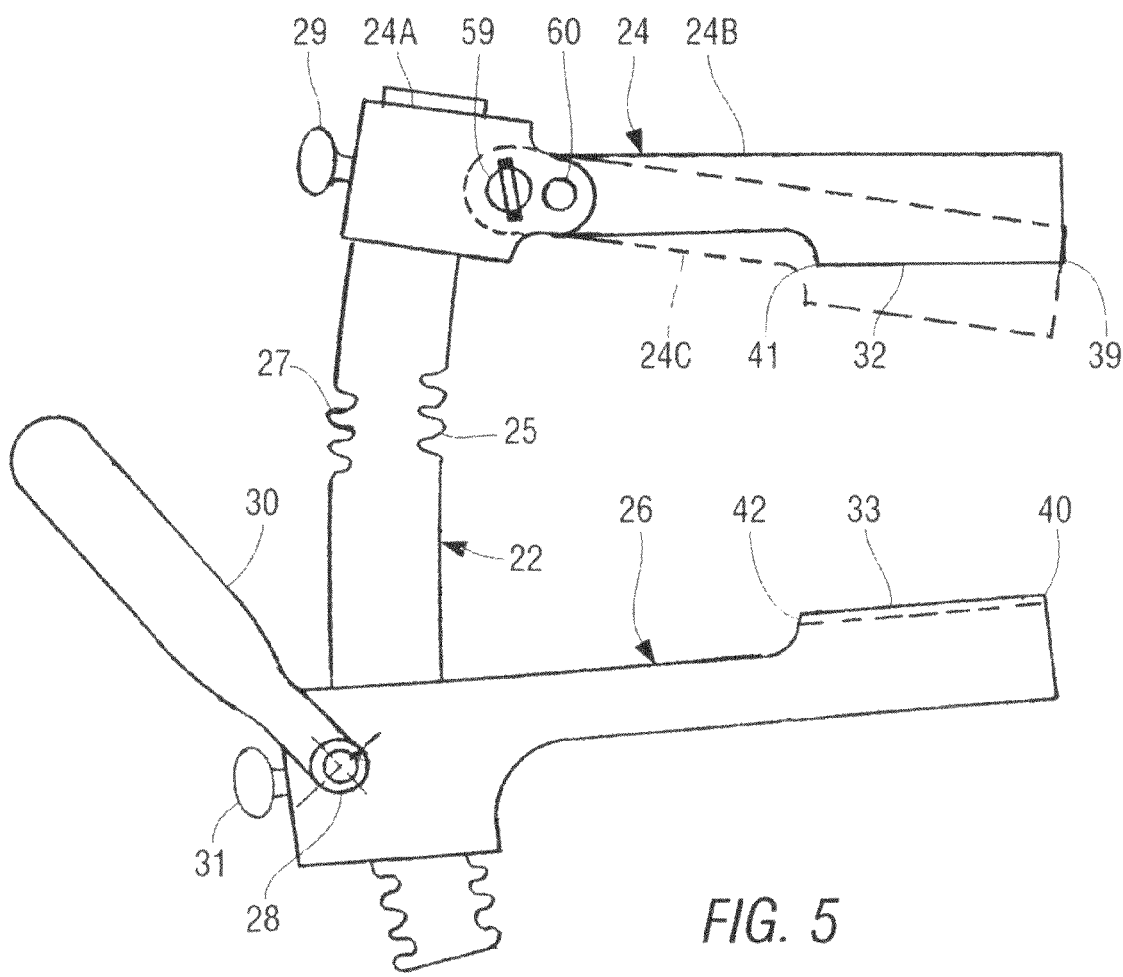
FIG. 5 is a plan view of the retractor assembled as shown in FIG. 2.

FIGS. 2 and 5 are views of the retractor 23 assembled in a second configuration, for use with the bar 22 near the abdomen. FIG. 2 is a perspective view of the retractor 23 so assembled, while FIG. 5 is a plan view thereof. It will be appreciated in this connection that the reversible nature of the preferred embodiment of the present invention is not a requirement of the invention but is the preferred embodiment for purpose of obtaining multiple uses for a single device. The positioning of the bar 22 can be chosen to provide the best view for the surgeon in a manner which is well known in the art. When the retractor 23 is used in the second orientation of FIG. 2, the blades 32, 33 are first placed into the severed sternum with the locking mechanism 60 holding the distal portion 24B of the first arm 24 in the inward position, as indicated by dashed lines 24C in FIG. 2 to have the blades together for initial positioning. After the arms 24, 26 are moved apart through a short distance, the distal portion 24B of the first arm 24 is moved to the medial position, in which it is shown in FIG. 2, to be subsequently held in place by the locking mechanism 59.

As is further shown in FIGS. 1, 3, 6 and 7, the bar 22 comprises teeth on sides 25 and 27, and arms 24 and 26 have blades 32 and 33, respectively. Arm 26 has a pinion 28, rotatably mounted within a hole 29, a crank 30, attached to the pinion 28, and a locking pin 31, which screws into hole 51 to secure the arm in a desired position. The proximal portion 24A has a locking pin 29 which secures it in place as well by screwing into hole 50 and impinging on the bar 22. Pinion 28 comprises individual teeth 44 adapted to mate with the teeth on bar 22 so that the arm 26 can be cranked open to spread open the chest. The locking pin 29 the arm with means for disconnecting said arm 24 from said bar 22 so that the arms can be reversed if desired to change the retractor 23 between the first configuration of FIG. 1 and the second configuration of FIG. 2, reversing the direction of curvature of the bar 22 relative to the arms 24, 26 to locate the bar either above or below the surgical area. Similarly, arm 26 can be removed from bar 22 so that it can be reversed between the first configuration of FIG. 1 and the second configuration of FIG. 2 Bar 22 is provided with a flattened area 43 onto which arm 24 may be secured. Arms 24 and 26 have slots 49 and 46, respectively, in which the bar 22 may be disposed in use.

As particularly shown in FIG. 3, the distal portion 24B of the first arm 24 is pivotally attached to the proximal portion 24A thereof by a hinge 59, including a pin 55 extending through a hole 61 in the proximal portion 24A and through a pivot hole 63 in the distal portion 24B. A locking pin or screw 60 extends through one of a plurality of holes 58 within the distal portion 24B of the first arm 24 and through holes 56 within the proximal portion 24A of the first arm 24. When the locking screw 60 extends through a central hole 53 within the plurality of holes 58, the distal portion 24B of the first arm 24 is held in the medial position, in which it is shown in FIGS. 1 and 2. When the locking screw 55 extends through a first lateral hole 64, the distal portion 24B is held in the inward position indicated by dashed lines 24C in FIGS. 2, 7. When the locking screw 60 extends through a second lateral hole 57, the distal portion 24B is held in an outward position (not shown).

In the preferred embodiment, the bar 23 is approximately 8 inches long, for adult sternal retractors and has a curvature of 40 degrees. The curvature of the bar 23 may be regular, that is, with a single radius of curvature or it may have multiple radii of curvature along its length to provide variation in the angle of the blades with respect to each other. The curvature of the bar can be of any desired radius, the preferred curvature providing an opening of 8 inches at the bottom of the sternum and an opening of 4 inches at the top of the sternum. The blades can be short, long, multiple or slightly angled to provide the desired secure opening of the sternum.

It will be obvious to a person of ordinary skill in the art that a number of modifications and changes can be made to the subject invention without departing from the spirit and scope of the present invention, which is defined by the claims appended hereto and all equivalents thereof.

I claim:

1. A method for sternal retraction, comprising:
   a) determining whether a sternal retractor is to be used with a curved bar nearer the abdomen or the head of a patient;
   b) in response to determining that the sternal retractor is to be used with the curved arm nearer the head of the patient, performing the following steps c) through f):
   c) assembling the sternal retractor with a pair of arms extending outward from a first side of the curved bar, wherein moving the arms apart along the bar causes the arms to be angled away from each other; and with a distal portion of one of the arms, pivotally mounted on a proximal portion of the arm, held in a first position so that blades of the arms are parallel to one another with the arms moved together along the curved bar,
   d) placing the sternal retractor on the patient with the curved bar nearer the head of the patient and with the blades of the arms extending toward the abdomen and into a split within the sternum of the patient;
   e) moving the distal portion to a second position, angled outward from the other arm; and
   f) spreading the arms along the curved bar to complete sternal retraction;
   g) in response to determining that the sternal retractor is to be used with the curved bar nearer the abdomen of the patient, performing the following steps g) through k):
   h) assembling the sternal retractor with a pair of arms extending outward from a second side of the curved bar, opposite the first side, wherein moving the arms apart along the bar causes the arms to be angled toward each other; and with a distal portion of one of the arms, pivotally mounted on a proximal portion of the arm, held in a third position, with the blades of the arms parallel to one another with the arms moved together along the curved bar,
   i) placing the sternal retractor on the patient with the curved bar nearer the abdomen of the patient and with the blades of the arms extending into a split within the sternum of the patient; and
   j) spreading the arms farther along the curved bar to complete sternal retraction.

2. The method of claim 1, wherein the first and third positions of the distal portion of one of the arms are the same position.

* * * * *